United States Patent
Wagner et al.

(10) Patent No.: US 11,219,538 B2
(45) Date of Patent: Jan. 11, 2022

(54) PROSTHESIS SHAFT RETAINING DEVICE AND SYSTEM COMPOSED OF PROSTHESIS SHAFT AND PROSTHESIS SHAFT RETAINING DEVICE

(71) Applicant: OTTO BOCK HEALTHCARE PRODUCTS GMBH, Vienna (AT)

(72) Inventors: Sonja Wagner, Vienna (AT); Alice Frey, Stockerau (AT); Walter Lunzer, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 106 days.

(21) Appl. No.: 15/747,133

(22) PCT Filed: Jul. 25, 2016

(86) PCT No.: PCT/EP2016/067659
§ 371 (c)(1),
(2) Date: Jan. 23, 2018

(87) PCT Pub. No.: WO2017/017057
PCT Pub. Date: Feb. 2, 2017

(65) Prior Publication Data
US 2018/0214284 A1    Aug. 2, 2018

(30) Foreign Application Priority Data
Jul. 29, 2015 (DE) .......................... 102015112406.8

(51) Int. Cl.
*A61F 2/78* (2006.01)
*A61F 2/54* (2006.01)
(Continued)

(52) U.S. Cl.
CPC .................. *A61F 2/78* (2013.01); *A61F 2/54* (2013.01); *A61F 2/80* (2013.01); *A61H 3/008* (2013.01);
(Continued)

(58) Field of Classification Search
CPC ...... A61F 2002/7862; A61F 2002/7837; A61F 2002/7868; A61F 2002/7881; A61F 2002/7893; A61F 2/80
(Continued)

(56) References Cited

U.S. PATENT DOCUMENTS 18,021 A * 8/1857 Selpho ............ A61F 2002/7862
623/58
396,061 A   1/1889 Allward
(Continued)

FOREIGN PATENT DOCUMENTS

CN    101808600 B    8/2010
CN    102985038 A    3/2013
(Continued)

OTHER PUBLICATIONS

PCT International Search Report for PCT International Patent Application No. PCT/EP2016/0676659, dated Oct. 13, 2016.

*Primary Examiner* — David H Willse
(74) *Attorney, Agent, or Firm* — Holland & Hart LLP

(57) ABSTRACT

A prosthesis socket retaining device and a system for securing a prosthesis socket to an upper extremity, comprising a securing part that can be guided along the torso below the axilla of the contralateral, unprovided side of a patient, and a coupling element which can be secured to the prosthesis socket and connected to the securing part, wherein the coupling element is displaceably mounted on the securing part.

21 Claims, 5 Drawing Sheets

(51) Int. Cl.
*A61H 3/00* (2006.01)
*A61F 2/80* (2006.01)
*A61F 2/50* (2006.01)

(52) U.S. Cl.
CPC . *A61F 2002/5036* (2013.01); *A61F 2002/546* (2013.01); *A61F 2002/785* (2013.01); *A61F 2002/7837* (2013.01); *A61F 2002/7862* (2013.01)

(58) Field of Classification Search
USPC .............................................. 623/58, 63, 33
See application file for complete search history.

(56) References Cited

U.S. PATENT DOCUMENTS

| | | | | |
|---|---|---|---|---|
| 809,797 | A | * | 1/1906 | Grogan ............... A61F 2/54 623/63 |
| 1,075,861 | A | | 10/1913 | Rowley |
| 1,206,753 | A | | 11/1916 | Desmore |
| 1,229,053 | A | | 6/1917 | Fekete |
| 1,338,155 | A | * | 4/1920 | Pringle ............... A61F 2/58 623/63 |
| 1,366,453 | A | | 1/1921 | Henning |
| 1,718,095 | A | | 6/1929 | Vradenburg |
| 2,157,747 | A | * | 5/1939 | Carmack ............... A61F 2/58 623/60 |
| 2,592,842 | A | | 4/1952 | Alderson |
| 3,188,655 | A | | 6/1965 | Cooper et al. |
| 4,258,441 | A | | 3/1981 | Bell |
| 5,403,268 | A | | 4/1995 | Clement |
| 8,323,355 | B2 | | 12/2012 | Latour |
| 2010/0210985 | A1 | | 8/2010 | Kuorak et al. |
| 2013/0092179 | A1 | | 4/2013 | Reinhardt et al. |

FOREIGN PATENT DOCUMENTS

| | | | | |
|---|---|---|---|---|
| DE | 321087 | C | | 5/1920 |
| GB | 111706 | A | | 12/1917 |
| GB | 206333 | A | | 11/1923 |
| GB | 2512504 | A | * | 10/2014 ............... A61F 2/78 |
| SU | 429810 | A1 | | 5/1974 |
| SU | 442796 | A1 | | 9/1974 |
| SU | 554861 | A1 | | 4/1977 |
| SU | 1066588 | A1 | | 1/1984 |
| SU | 1780508 | A3 | | 1/1990 |
| SU | 1554907 | A1 | * | 4/1990 ..... A61F 2002/7862 |

* cited by examiner

PROSTHESIS SHAFT RETAINING DEVICE AND SYSTEM COMPOSED OF PROSTHESIS SHAFT AND PROSTHESIS SHAFT RETAINING DEVICE

TECHNICAL FIELD

The invention relates to a prosthesis socket retainer for securing a prosthesis socket to an upper extremity, with a securing part which can be guided along the torso under the axilla of the contralateral, intact side of a patient, and with a coupling element which can be fastened to the prosthesis socket and can be connected to the securing part, and also a system composed of a prosthesis socket and of such a prosthesis socket retainer. The prosthesis socket retainer is suitable and provided in particular for securing upper arm sockets to an upper arm stump.

BACKGROUND

U.S. Pat. No. 5,403,268 A relates to an orthosis with which dislocated shoulders are supported. A cuff is placed around the upper arm, and a shoulder strap extends round the torso from the collarbone and under the opposite armpit. The cuff is secured to the shoulder strap by belts and buckles. Such a device is not provided for prostheses.

After loss of the forearm or in the absence of the forearm, it is necessary to provide a prosthesis in which a gripping element or a prosthetic hand is secured to a forearm element. Drive devices, control devices and energy storage devices can be arranged inside the forearm element. To secure the prosthetic hand and the forearm part, these components are generally mounted in an articulated manner on an upper arm socket, which is secured to the remaining upper arm stump of the patient. An upper arm socket can be secured to the torso via complex belt constructions in which the belts are guided along the torso. Belts or straps are guided along the contralateral side of the torso and secured to the prosthesis socket, such that the upper arm socket is held securely on the patient.

A further possibility for securing a prosthesis to an upper arm stump lies in what is called suction socket technology, in which a liner made of a plastic or silicone material is pulled over the upper arm stump. The prosthesis socket made of a dimensionally stable material serves to receive the liner with the stump. The liner is held on the socket by mechanical locking means or by negative pressure. A possible problem here is that the adhesion force applied between the liner and the stump may be inadequate to hold the prosthesis on the stump under a tensile load. Changes in the volume of the stump may lead to a reduction of the adhesive force. Furthermore, patients may experience a degree of uncertainty if the arm prosthesis is held on the stump exclusively via the liner.

SUMMARY

The object of the present invention is to make available a prosthesis socket retainer and a system composed of prosthesis socket and prosthesis socket retainer which ensure that the prosthesis socket is safely secured to the patient and which also permit free mobility of the shoulder joint.

According to the invention, this object is achieved by a prosthesis socket retainer having the features of the main claim, and by a system composed of a prosthesis socket retainer and a prosthesis socket in accordance with the additional independent claim. Advantageous embodiments and developments of the invention are disclosed in the subclaims, the description and the figures.

In the prosthesis socket retainer for securing a prosthesis socket to an upper extremity, with a securing part which can be guided along the torso under the axilla of the contralateral, intact side of a patient, and with a coupling element which can be fastened to the prosthesis socket and can be connected to the securing part, provision is made that the coupling element is mounted displaceably on the securing part. The prosthesis socket, particularly in the embodiment as an upper arm socket, is fixed to the upper body of the patient via a securing part. The securing part is guided under the axilla on the intact side of the patient and thereby ensures that tensile forces from the prosthesis socket retainer, which are exerted on the securing part, are taken up via the torso and not via the neck region. The coupling element is secured or can be secured on the prosthesis socket and is mounted displaceably on the securing part, as a result of which the mechanical fastening of the prosthesis socket to the securing part is ensured and, moreover, the free mobility in the shoulder joint on the treated side remains unimpaired. The humerus moves with its joint head in the joint socket of the shoulder blade, wherein only a quarter of the joint head is enclosed by the socket, which fact permits great mobility of the shoulder joint. Furthermore, a joint capsule is present which has a strengthening ligament in order to hold the joint head in the joint socket. The shoulder joint has no further ligament arrangements, and the joint is held together solely by the musculature. The shoulder joint is therefore the most mobile joint, and its position on the trunk is also variable via the collarbone. This high degree of mobility means, among other things, that conventional fastening of prosthesis sockets to the shoulder using belts and buckles leads to restrictions on movement, since these belts cannot compensate the mobility. By virtue of the coupling element being mounted displaceably on the securing part, it is possible to reduce the uncertainty felt by the patients by providing mechanical fastening, but without restricting the mobility. The coupling element thus compensates the relative movement between the securing part and the prosthesis socket, such that a physiological swinging of the treated arm is permitted.

In a development of the invention, provision is made that the coupling element can be secured releasably to the prosthesis socket. The releasability of the coupling element has the advantage that it can be produced and adapted independently of the prosthesis socket. The coupling element, if appropriate with the necessary devices for fastening to the prosthesis socket, can be cleaned independently of the prosthesis socket, for example by washing.

The coupling element can be secured with form-fit engagement to the prosthesis socket, i.e. can be arranged directly on the prosthesis socket, for example via hook-and-loop fasteners, buckles or other connecting elements. In the case of a one-piece design of the coupling element, it is likewise possible to provide a funnel-shaped receptacle in which the prosthesis socket is inserted or which is placed around the prosthesis socket, such that the prosthesis socket is prevented from slipping out in the distal direction. The coupling element can likewise be arranged on a cuff or sleeve which is secured or can be secured releasably to the prosthesis socket. In this way, the prosthesis socket retainer can be easily fitted in place by the prosthesis user himself, since the coupling element can be placed around the prosthesis socket and can be secured thereon via belts, buckles or hook-and-loop fasteners. It is likewise possible to configure the cuff or sleeve with a closed cross section, wherein the coupling element is then secured or can be secured to the cuff or is formed thereon.

The coupling element can have a multi-part design, for example composed of a strap and the abovementioned cuff or sleeve, which then together form the coupling element. Alternatively, the coupling element is a tensioning means or strap which is guided over the collarbone in the direction of the back, into the region of the thoracic spine, is deflected at a deflection device and is guided dorsally to the prosthesis socket and fastened there. The coupling element can have a flexible tensioning element, for example a strap, a belt or another tensioning element, which is either secured directly to the prosthesis socket or fastened to the prosthesis socket via the cuff or sleeve, which can be part of the coupling element. The tensioning element is preferably flexible and inelastic in order to ensure that the prosthesis socket is safely assigned to the securing part. The tensioning element can be guided movably, in particular displaceably, in a guide that is fastened or formed on the securing part. The guide can be formed, for example, by a recess in the securing part, or the guide can alternatively be fastened as a separate component to the securing part, for example in the form of a loop, a ring or a similar guide, and deflection element made of metal or plastic which has a preferably closed hollow cross section in order to guide the tensioning element and also to allow the tensioning element to shift relative to the guide. The coupling element is freely movable inside the guide in order to permit the shoulder movement.

The coupling element can be guided displaceably in a protective sleeve or on a protective support in order to avoid or prevent friction between the torso, or shoulder, and the coupling element. In the fitted state of the prosthesis socket retainer, the protective sleeve or the protective support bears on the torso or at the torso, wherein the prosthesis socket retainer can be worn both directly on the skin and also over clothing. The protective sleeve or protective support avoids friction between the coupling element and the underlying substance, whether textile or the skin.

In the fitted state, the coupling element is preferably guided along the front aspect and the rear aspect of the treated shoulder, wherein the region of the joint head can remain clear. A front part of the coupling element extends across the collarbone in the direction of the shoulder blade, is coupled to the securing part there by the guide, and is then guided in the dorsal region of the axilla back in the direction of the prosthesis socket. Therefore, by way of the coupling element, the front of the prosthesis socket retainer or of the prosthesis socket is connected to the back of the prosthesis socket retainer or of the prosthesis socket and is coupled via the displaceable mounting and deflection on the securing part in such a way that the respective forward and rearward movement of the arm and of the prosthesis socket relative to the torso is compensated by a displacement of the coupling element.

The securing part can be designed as a planar blank and can have an opening as a passage for an arm. Alternatively, the securing part can be configured with connecting elements at the ends, as a result of which the securing part is easier to fit in place and adapt to the individual. By virtue of the opening serving as a passage for an arm, it is possible that the securing part can be easily fitted in place since the arm of the contralateral side has to be easily guided through the arm opening in order to fit the securing part in place. If connecting elements are provided on the securing part, these are arranged on projections or regions of the securing part that can be connected to each other, such that an opening forms or such that the securing part can be placed around the shoulder, wherein a part of the securing part is guided under the axilla.

The securing part is configured such that, in the fitted state, it is mainly guided dorsally, i.e. only a small part of the securing part is guided frontally in the shoulder region, whereas most of the securing part is positioned dorsally. In the frontal shoulder region, the securing part is preferably configured like a strap in order to impair the mobility of the shoulder joint as little as possible, if indeed at all. In the region of the axilla, the securing part can have a padding, for example in the form of a filling with bead-like plastics which adapt very well to the anatomy of the user and follow the movements of the arm.

In a development of the invention, provision is made that the securing part, in the fitted state, extends dorsally beyond the median plane in the direction of the prosthesis socket. The guide for the coupling element is likewise positioned dorsally in the fitted state of the prosthesis socket retainer, such that the patient does not experience restricted mobility in the chest region.

The securing part and/or the coupling element can be made of a textile material, a spacer knit and/or foam material, which permit simple working, an easy fit and good washability.

The coupling element can be configured or guided as a loop, wherein it is either connected directly to the prosthesis socket or fastened via a fastening portion or a fastening device such as a sleeve, cuff, clasp or the like.

The system according to the invention is composed of a prosthesis socket, in particular for receiving an upper arm stump, and of a prosthesis socket retainer as described above.

BRIEF DESCRIPTION OF THE DRAWINGS

Illustrative embodiments of the invention are explained in more detail below with reference to the accompanying figures, in which.

DETAILED DESCRIPTION

Figure 1:
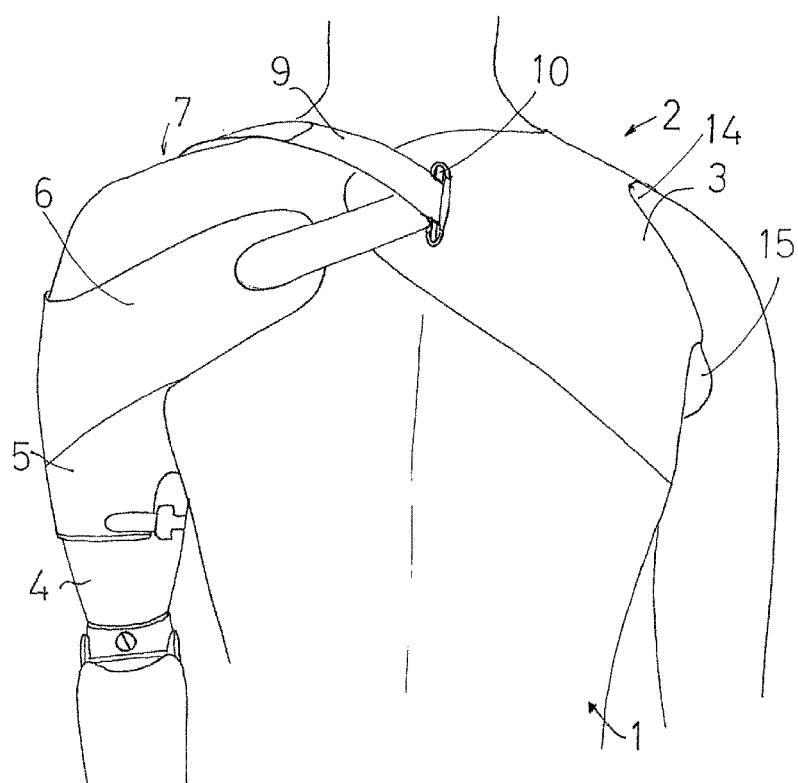
FIG. 1 shows a fitted prosthesis socket retainer in a rear view.
Figure 2:
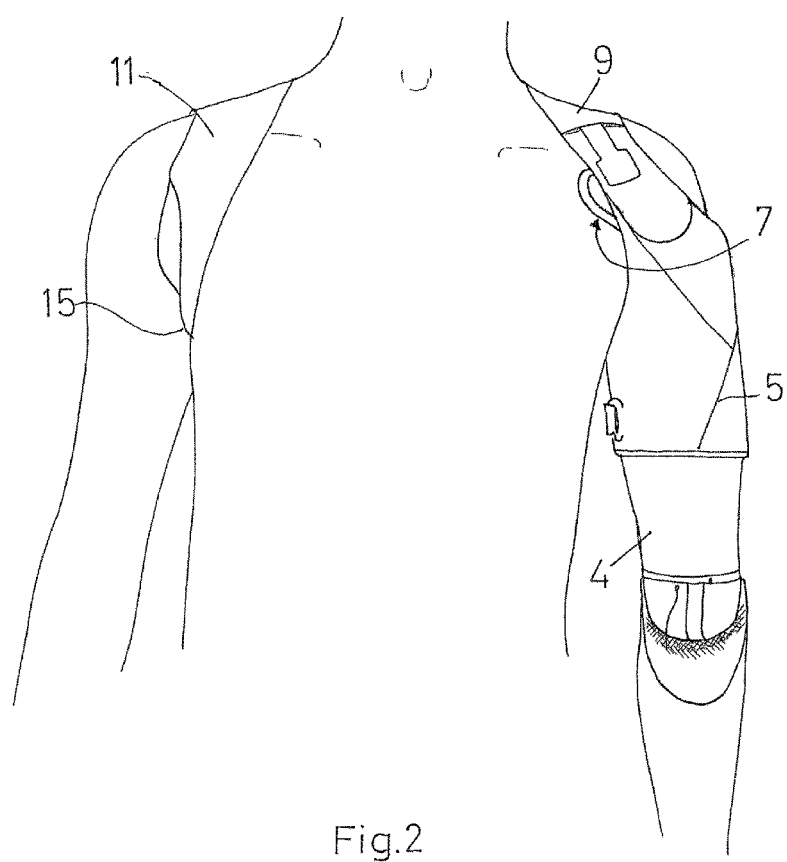
FIG. 2 shows a fitted prosthesis socket retainer in a front view.

FIG. 1 shows a rear view of a prosthesis socket retainer which is fitted on a patient. The prosthesis retainer has a securing part 2 which, in the illustrative embodiment shown, is composed of a textile main body in which an opening 14 is formed as a passage for an arm. In the fitted state, the securing part 2 is thus guided under the axilla on the intact side. In the axilla region, a padding 15 is arranged which, as padding material, can have foam or bead-like plastics, for example of polystyrene. The padding 15 ensures that the blood circulation is not obstructed in this region, and it also provides adaptation to the anatomy of the user, as a result of which the movement of the intact arm is restricted minimally, if indeed at all. The securing part 2 can be configured as a one-piece main body that is cut to size from a sheet of material. As regards a suitable fit, it is advantageous if the securing part 2 is produced from a planar blank, wherein the blank has a rear portion 3 and a belt-like or strap-like front portion 11, wherein the front portion 11 is shown in FIG. 2. In the main blank, the rear portion 3 and the front portion 11 can have unconnected ends, which are advantageously connected to each other, for example by stitching, in the region of the axilla, in order to obtain a shape adapted to the anatomy of the shoulder. The rear portion 3 has a substantially larger surface area than the front portion 11 and, in the illustrative embodiment shown, extends medially from the trapezius muscle, across the shoulder blade and beyond the median plane, reaching laterally as far as the posterior axilla region. By means of the suitable stitching of the two free ends in the axilla region, the opening 14 is formed as a passage for an arm, such that, in the fitted state, the securing part 2 lies across a large surface area in the back region, the front portion extends over the collarbone and under the axilla, and the securing part 2 is thus fastened securely to the torso 1 of the patient.

The rear portion 3 extends beyond the median plane in the direction of the treated upper extremity, where a prosthesis socket 4 is fastened to an upper arm stump. The fastening can be effected, for example, with the aid of a prosthesis liner which is pulled over the upper arm stump (not shown). The prosthesis liner can be held firmly on the prosthesis socket 4 either mechanically or by negative pressure.

A sleeve 5 or cuff is arranged on the outside of the prosthesis socket 4 and is placed tightly around the outside of the prosthesis socket 4 via a strap or another securing element. Both the prosthesis socket 4 and the sleeve 5 are widened conically in the proximal direction, wherein the distal end of the sleeve 5 has a smaller circumference than the proximal end of the prosthesis socket 4, such that the prosthesis socket 4 cannot be moved through the distal opening of the sleeve 5. An anti-slip coating can also be arranged on the inside of the sleeve 5, such that the sleeve 5, once fitted in place, is fixed securely on the prosthesis socket 4. The sleeve 5 can also be configured with an open cross section, that is to say rather in the form of a cuff, wherein the open cross section can be closed with the aid of closing means, for example hook-and-loop fasteners, belts or other form-fit elements.

As is shown in FIG. 1, a dorsal continuation 6 is secured or formed on the sleeve 5 and extends in the medial direction toward the securing part 2. The dorsal continuation 6 extends substantially across the shoulder blade in the direction of the neck region of the patient. As is shown in FIG. 2, a frontal continuation 7 is secured or formed on the front of the sleeve 5 and extends in the anterior region of the shoulder in the direction of the collarbone of the treated side. A coupling element 9 in the form of a flexible, preferably inelastic strap is secured to the front continuation 7 and to the dorsal continuation 6. The coupling element 9 extends across the collarbone on the treated side in the direction of a guide 10, which is configured in the form of a bridge, a web, a ring or a loop on the securing part 2. The coupling element 9 extends around the guide 10, i.e. is only deflected and is not impaired in terms of its displaceability relative to the guide, and is fastened to the dorsal continuation 6, for example stitched, or reversibly fixed with a hook-and-loop fastener. The coupling element 9 is mounted displaceably on the guide 10, that is to say the coupling element is not fastened to the guide 10 and is instead mounted so as to be movable therein. Depending on the tensioning direction, the coupling element 9 can be moved in one direction or the other.

In the illustrative embodiment shown, the guide 10 is arranged in the region of the spinal column, i.e. on the median plane, when the prosthesis socket retainer is fitted in place.

In the case of the coupling element 9 being secured releasably to the dorsal continuation 6 or to the frontal continuation 7, it is possible to adjust the effective length of the coupling element 9 and to adapt the prosthesis socket retainer individually to the particular patient.

Figure 3:
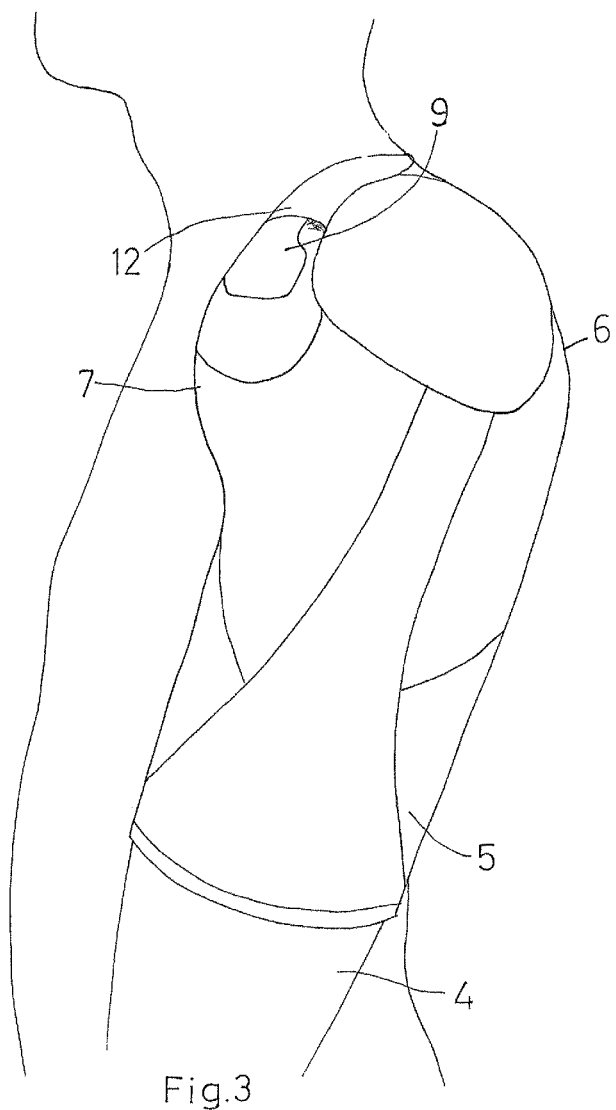
FIG. 3 shows a fitted prosthesis socket retainer in a side view.

FIG. 3 shows the fitted prosthesis socket retainer in a side view. It will be seen that the dorsal continuation 6 and the frontal continuation 7 enclose the shoulder joint dorsally and frontally, but leave the shoulder joint itself free and secure the prosthesis socket 4 via the sleeve 5. In the illustrative embodiment shown, the coupling element 9 is guided in a protective sleeve 12 which is fitted in the neck region of the patient in order to avoid direct chafing of the skin by the coupling element 9 when the treated arm is moved.

Figure 4:
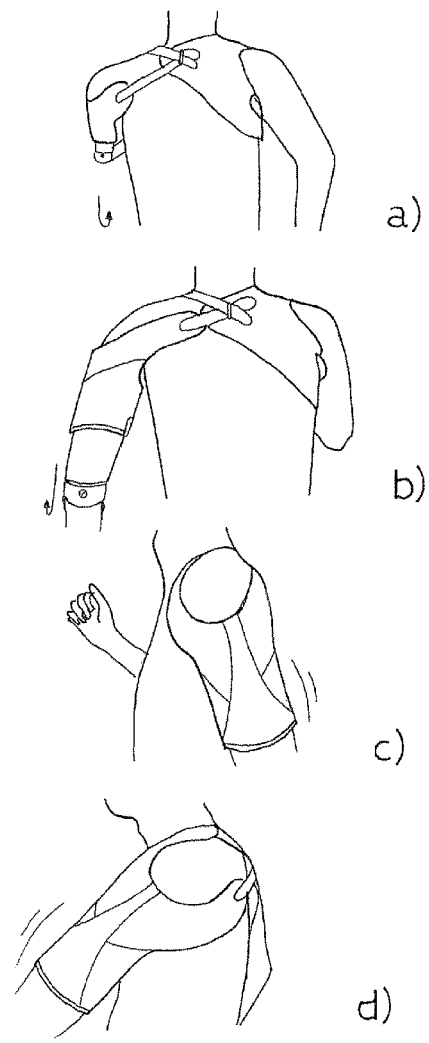
FIGS. 4a-4d show prosthesis socket retainers in different positions.

FIGS. 4a-4d show different states of movement or phases of movement during the use of the prosthesis socket retainer. In FIG. 4a, the arm prosthesis is swung forward, which has the effect that the front continuation 7 is moved in the direction of the collarbone. Correspondingly, the dorsal continuation 6 is moved away from the guide 10. This movement has the effect that the coupling element 9 slides inside the guide 10 and ensures the free mobility of the prosthesis.

FIG. 4b shows the prosthesis socket retainer in a state in which the elbow or arm is swung rearward, the dorsal continuation 6 is thereby shifted in the direction of the guide 10, and the coupling element 9 slides inside the guide 10, such that the front continuation 7, despite the connection to the dorsal continuation 6, is able to move away from the collarbone.

The position according to FIG. 4b is shown in the side view in FIG. 4c; the position according to FIG. 4a is shown in the side view in FIG. 4d. It will be clearly seen that the dorsal continuation 6 is guided forward in a movement in the shoulder joint, whereas the frontal continuation 7 is moved via the shoulder blade in the direction of the guide 10. The movement of the frontal and dorsal continuations 6, 7 is fixed by the coupling element 9 and by the almost fixed position of the guide 10 in the region of the spinal column. The guide 10 is positioned at a location where no shifting or only slight shifting of the guide 10 relative to the torso 1 is expected, since it is positioned approximately at the transition from the cervical spine to the thoracic spine or in the upper third of the thoracic spine.

Figure 5:
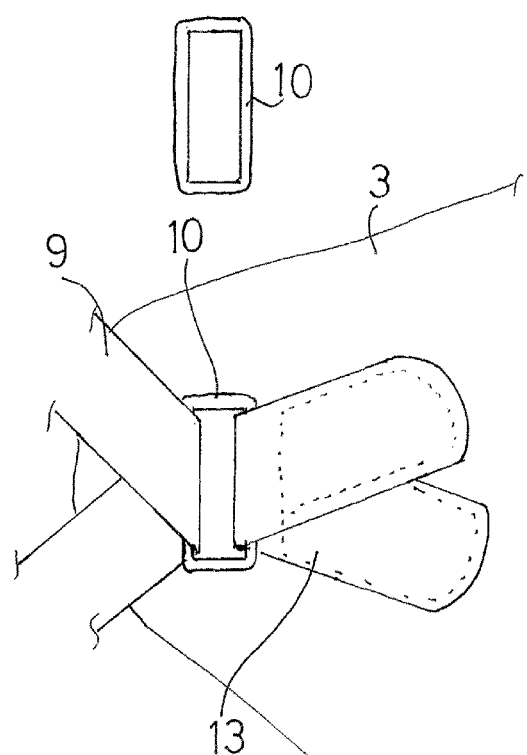
FIG. 5 shows details of the prosthesis socket retainer.

FIG. 5 shows a detailed view of the securing part 2 with the rear portion 3 and with the guide 10 fastened there. In the illustrative embodiment shown, the guide is configured as a square wire element with a substantially closed cross section. By way of a flap of fabric 13, the guide 10 is fixed on the securing part 2 in such a way as to be foldable but substantially stable in position. The textile element 13 can be adhesively bonded or sewn on or welded on. In principle, it is also possible to vary the position of the guide 10 on the securing part 2 in order to permit adaptation to the patient.

The coupling element 9 is placed around a free branch of the guide 10 and can be moved thereon in a sliding guide, such that length compensation and free mobility of the coupling element 9 is ensured. The upper view shows the shape of the guide 10 on its own.

As an alternative to a separate guide element 10 made of a wire or plastic, the guide 10 can also be formed inside the securing part 2 by two slits through which the coupling element 9 is guided. The embodiment with two slits has the advantage that the coupling element 9 is guided for the most part along the top and on the surface of the securing part 2 in order to substantially avoid a chafing movement on the skin or a fabric.

By way of the coupling element, the prosthesis retainer according to the invention fastens the prosthesis socket 4 mechanically to the torso 1 of the prosthesis user via the securing part 2. In view of the fact that only relatively narrow straps or strap-like portions are guided along the frontal chest region and the coupling element 9 is deflected in the guide 10 on the back, advantageously in the region of the upper thoracic spine, the physiological gait pattern of the user is not adversely affected since the movement in the shoulder joints is not restricted. Moreover, the prosthesis arm is allowed to swing too, and the mobility of the contralateral, intact arm is not restricted. The entire prosthesis retainer is removable from the prosthesis socket 4, and it can therefore be washed and easily cleaned. The securing part 2 can be separated from the remaining part of the prosthesis retainer assigned to the prosthesis, since the coupling element 9 is released from the cuff or the sleeve 5 with its dorsal or frontal continuations 6, 7. By virtue of this modular design, it is possible to produce prefabricated cuffs 5 or sleeves which are adapted to different prosthesis sockets 4 and to freely combine these with likewise prefabricated securing parts 2, depending on which configuration best suits the particular patient.

It is also possible in principle that the coupling element 9 is fixed directly on the prosthesis socket 4, i.e. no outer fastening sleeve 5 or cuff is present that completely surrounds the outside of the prosthesis socket 4. Instead, the coupling element 9 can be fixed directly to the prosthesis socket 4 via form-fit elements or hook-and-loop fasteners, if appropriate in a protective sleeve 12 or on a protective support in order to avoid direct rubbing of the movable coupling element 9 on the skin. If possible, the securing part 2 is designed with such a large surface area that there is no direct contact or almost no direct contact between the coupling element 9 and the skin, particularly in the region of the collarbone on the treated side.

The swinging of the prosthesis arm during walking is favored by the strap guide, i.e. the sliding guide of the coupling element 9, in the back region. The prosthesis socket retainer can be put on and taken off independently by the patient and can be adapted by simple measures to different prosthesis sockets 4. The material of the securing part 2 and also of the cuff 5 with the frontal and dorsal continuations 6, 7 can be a textile material, for example a 3D spacer knit, and it is likewise possible to use foam materials, for example open-pore foams, in order to ensure a high degree of wearing comfort while minimizing the build-up of moisture.

The invention claimed is:

1. A prosthesis socket retainer to secure a prosthesis socket to an upper extremity, the prosthesis socket retainer comprising:
a securing part including a front portion and a rear portion, the front portion configured to be guided along a patient's torso over the collarbone and under an axilla region of a contralateral, intact side of the patient, in contact with a side of the patient, and the rear portion extending across a median plane of the patient in the direction of the upper extremity of the patient;
a coupling element selectively attachable to and detachable from the prosthesis socket, and connected displaceably to the securing part, the coupling element being solely slidably connected to the securing part so as to adapt to movement of the upper extremity, wherein the coupling element is a sleeve or cuff that is releasably secured to the prosthesis socket.

2. The prosthesis socket retainer as claimed in claim 1, wherein the coupling element is releasably connected to the prosthesis socket.

3. The prosthesis socket retainer as claimed in claim 1, wherein the coupling element has a multi-part design.

4. The prosthesis socket retainer as claimed in claim 1, wherein the coupling element has a flexible tensioning element which is guided movably in a guide, the guide being fastened or formed on the securing part.

5. The prosthesis socket retainer as claimed in claim 1, wherein the coupling element is guided displaceably in a protective sleeve or on a protective support, and the protective sleeve or protective support bears on the torso in a fitted state.

6. The prosthesis socket retainer as claimed in claim 1, wherein, in a fitted state, the coupling element is guided along the front aspect and the rear aspect of a shoulder of the patient.

7. The prosthesis socket retainer as claimed in claim 1, wherein the securing part is designed as a planar blank and has an opening as a passage for an arm or is configured as a loop with connecting elements at ends of the loop.

8. The prosthesis socket retainer as claimed in claim 1, wherein the securing part has a padding in the axilla region.

9. The prosthesis socket retainer as claimed in claim 1, wherein the securing part, in the fitted state, extends dorsally beyond a median plane in a direction of the prosthesis socket.

10. The prosthesis socket retainer as claimed in claim 1, wherein at least one of the securing part and the coupling element is produced from at least one of a textile material, a spacer knit and foam material.

11. The prosthesis socket retainer as claimed in claim 1, wherein the coupling element is configured as a loop.

12. A system composed of a prosthesis socket retainer as claimed in claim 1 and the prosthesis socket.

13. The prosthesis socket retainer as claimed in claim 1, wherein the coupling element is guided in a recess, guide or eyelet.

14. A prosthesis socket retainer, comprising:
a securing part configured to be guided along a patient's torso under an axilla region of a contralateral of the patient, and in contact with a side of the torso, wherein the securing part extends along a chest of the patient and under an armpit of the patient;
a coupling element configured to be selectively attached to and detached from a prosthesis socket and the securing part, the coupling element being freely slidable relative to the securing part so as to adapt to movement of the prosthesis socket when mounted to an upper extremity of the patient, wherein the coupling element extends in front of and behind a shoulder of the patient, and wherein the coupling element is secured with form-fit engagement to the prosthesis socket or is arranged on a cuff or sleeve that is releasably secured to the prosthesis socket.

15. The prosthesis socket retainer as claimed in claim 14, wherein the coupling element is releasably connected to the prosthesis socket.

16. The prosthesis socket retainer as claimed in claim 14, wherein the coupling element has a multi-part design.

17. The prosthesis socket retainer as claimed in claim 14, wherein the coupling element has a flexible tensioning element which is guided movably in a guide, the guide being fastened or formed on the securing part.

18. The prosthesis socket retainer as claimed in claim 14, wherein the coupling element is guided displaceably in a protective sleeve or on a protective support, and the protective sleeve or protective support bears on the torso.

19. The prosthesis socket retainer as claimed in claim 14, wherein, in a fitted state, the coupling element is guided along a front aspect and a rear aspect of a shoulder of the patient.

20. The prosthesis socket retainer as claimed in claim 14, wherein the coupling element is solely slidably connected to the securing part.

21. The prosthesis socket retainer as claimed in claim 14, wherein the coupling element is guided in a recess, guide or eyelet.

* * * * *